United States Patent [19]
Johnson et al.

[11] Patent Number: 5,831,161
[45] Date of Patent: Nov. 3, 1998

[54] SNOW STRENGTH PENETROMETER

[75] Inventors: Jerome B. Johnson, Fairbanks, Ak.; Martin Schneebeli, Davos Dorf, Switzerland

[73] Assignee: The United States of America as represented by the Secretary of the Army, Washington, D.C.

[21] Appl. No.: 850,160

[22] Filed: May 2, 1997

[51] Int. Cl.$^6$ ........................................ G01N 3/42
[52] U.S. Cl. ............................................. 73/432.1
[58] Field of Search ................. 73/866, 81–85, 73/432.1

[56] References Cited

U.S. PATENT DOCUMENTS

| | | | |
|---|---|---|---|
| 4,094,188 | 6/1978 | Bellouin et al. | 73/81 |
| 4,332,160 | 6/1982 | Baragar et al. | 73/84 |
| 5,433,215 | 7/1995 | Athanasiou et al. | 73/81 |

FOREIGN PATENT DOCUMENTS

| | | | |
|---|---|---|---|
| 195 03 017 A1 | 9/1995 | Germany . | |
| 187159 | 10/1922 | United Kingdom | 73/84 |

OTHER PUBLICATIONS

ASAE, (1995) Soil cone penetrometer. In ASAE standards 1995, St. Joseph, Michigan: American Society of Agricultural Engineering, ASAE S 313.2, p. 683.
Bader, H., R. Haefeli, E. Bucher, J. Neher, O. Eckel and C. Thams (1954) Snow and its metamorphism. Snow Ice and Permafrost Research Establishment, p. 135.
Bradley, C.C. (1966) The snow resistograph and slab avalanche investigations. In *International Symposium on Scientific Aspects of snow and Ice Avalanches*, Davos, Switzerland, 5–10 Apr. 1965. International Association of Hydrological Sciences, International Union of Geodesy and Geophysics, Publ.No.69pp. 251–260.
Dowd, T. and R.L. Brown (1986) A new instrument for determining strength profiles in snow cover. Journal of Glaciology, 32(111): pp. 299–301.
Fritton, D.D. (1990) A standard for interpreting soil penetrometer measurements. Soil Science, 105 (2): pp. 542–551.
Haung, A.–B., M.Y. Ma and J.S. Lee (1993) A micro mechanical study of penetration tests in granular material. Mechanics of Materials, 16(1 & 2):pp.133–139.
Navarre, J.P., A. Taillefer and E. Flavigny (1994) Le "Panda Neige".*Neige et Avalanches*, 66:pp. 8–14,(Franke).
Olsen, H.J. (1992) article entitled "Sensing of aggregate size by means of horizontal minipenetrometer", *Soil &Tillage Research*, 24:pp. 79–94.
Shoop, S. and S. Taylor (1990) Microscopic observations of snow deformation. In *The 47th Eastern Snow Conference*, Bangor, Maine,. pp. 27–38.

*Primary Examiner*—Robert Raevis
*Attorney, Agent, or Firm*—Luther A. Marsh

[57] ABSTRACT

The snow penetrometer apparatus with data acquisition hardware measure force required to push a small dimension tip member into a snow surface at constant speed that: i) is less than 5 mm in diameter or cross-sectional width, ii) has up to a 90° included angle; iii) has a flared tip and iv) is extended beyond a penetrating head. The penetrometer tip member has a high elastic modulus and is attached through a connecting rod to a stiff penetrating head that is in turn attached to a driving rod. The penetrometer tip member acts through a force sensing transducer. The driving rods are a meter in sectional length that can be joined together for snow penetration up to several meters. The depth of snow penetration is determined by measuring movement of a drive motor or drive rods. The penetrometer tip member is driven downward by a constant speed rotary or linear motor. Two different penetrating head designs are used. The first penetrating head design has a diameter slightly larger than the driving rod to reduce sidewall friction. The second penetrating head design has the same diameter as the driving rod to reduce the volume of influence ahead of the penetrating head. Both heads are low included angle of 30° or less. A measured event of the penetrometer tip encountered force is recorded and correlated with depth of penetration for later analysis to determine its mean value and variation about this mean value to obtain an index measure of inter-grain bonding and snow grain size.

22 Claims, 4 Drawing Sheets

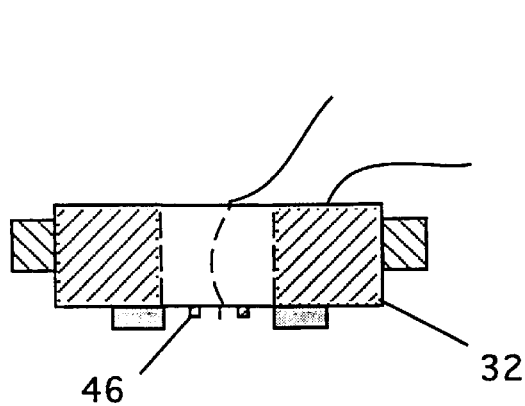
FIG. 3A
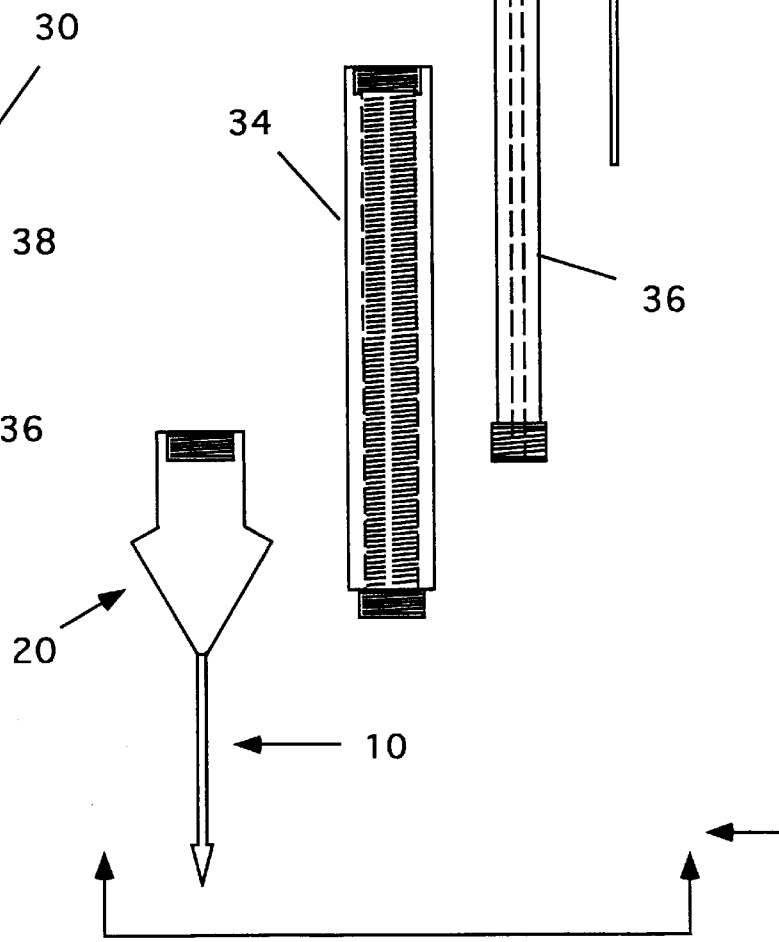
FIG. 3B
FIG. 3C
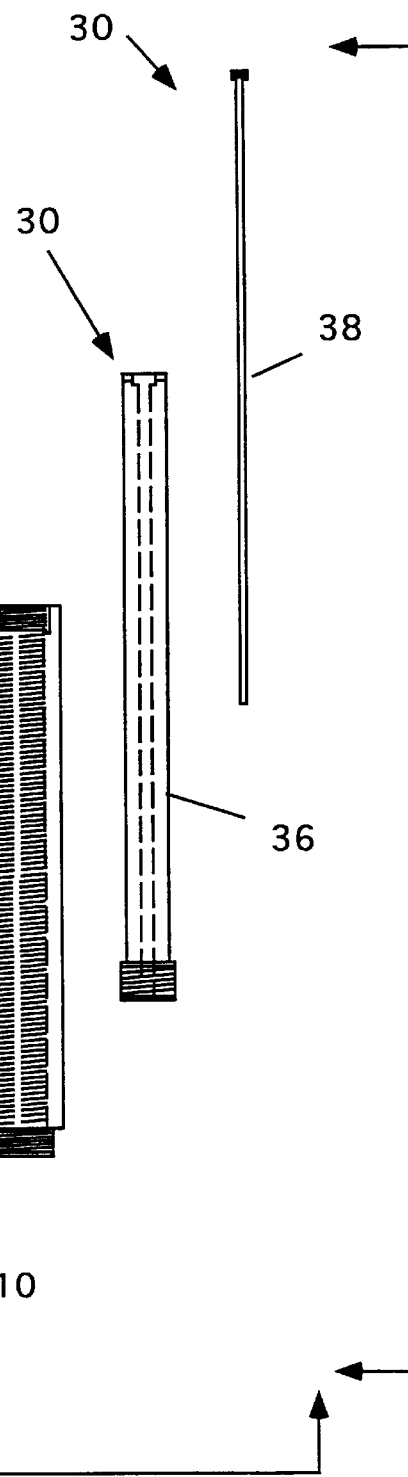

SNOW STRENGTH PENETROMETER

STATEMENT OF GOVERNMENT INTEREST

The invention described herein may be manufactured and used by or for the United States Government for governmental purposes without the payment of any royalties thereon.

FIELD OF THE INVENTION

The invention pertains to a device for providing data about the mechanical response of snow when external loads are applied thereto. In particular, the invention provides data related lo the internal structure of snow for determining an index of grain bond strength, grain shape/size and internal layering of the snow that affects it's, mechanical response to external loads.

BACKGROUND OF THE INVENTION

Devices that provide data about the mechanical response of a snow surface when external loads are applied to that surface are used for building snow roads, snow runways, or structural foundations on the snow. Such devices are also used to determine: i) deformation of a snow acting upon a structure which is a secondary factor of that snow's weight on the structure; ii) a snow's internal structure for environmental and physical studies of snow's intrinsic properties; iii) a vehicle's ability to move through snow; and iv) stability of a snow covered surface as related to potential avalanche hazards.

The mechanical response of a snow surface when an external load is applied thereto is a function of several factors including: i)temperature, ii) rate of deformation or loading, iii) snow density and iv) internal structure, i.e. it's, grain size distribution, grain shape, inter-granular bonding, and internal layering. The invention herein provides data on the internal structure of snow for determining this index of grain bond strength, grain shape/size and information about internal layering of the snow that bears upon the mechanical response thereof for use in connection with the above listed applications.

Existing devices used for some of the above measurements include penetrometers designed for snow use. These include: is impact driven rods with large diameter tips that are 35–40 mm and ii) hand or spring pushed penetrometer rods with large penetrating tip diameters that are greater than 5 mm. The hand driven penetrometers measure force of penetration using "proving rings" or electronic force transducers. These devices are not intended to penetrate a snow covered surface at constant speed. Such use yields inconsistent results as to measured force of penetration versus depth of penetration of the penetrometer. More significantly, these types of penetrometers usually induce frictional effects during a penetration such operation resulting in a cone of snow material being pushed in front of the penetrating tip. This in turn reduces resolution of observed data of thinner snow layers, thus lessening data reliability indicative of the index of snow grain bond strength.

Navarre et al. 's article entitled Le "Panda Neige". *Neige et Avalanches*, 1994, 66:pp.8–14, teaches of an impact driven rod device that calculates penetration resistance from the energy of impact and displacement of the driving rod in the snow. Limitations of this device and method include inaccuracies that result from: i)applied impact energy does not all go into the tip penetration and ii) such impacts produce rapid acceleration of the driving rod member that inherently introduces unwanted inertial effects. Inaccuracies result since the weight of the penetrometer is supported by the snow where sudden collapse in weak subsurface snow regions resulting in acceleration of the penetrometer tip. The instant invention overcomes these inaccuracies by use of a penetrometer device that penetrates at a constant speed where the snow's resistance force is directly measured.

Examples of hand driven/spring operated push rod snow/soil penetrometer devices with large tip angles include: i) American Society of Agricultural Engineering Standard: "Soil cone penetrometer, "1995 ASAE S313.2, p.683; ii) Shoop et al.'s article entitled "Microscopic observations of snow deformation." In *The 47th Eastern Snow Conference*, Bangor, Me.,1990, pp.27–38; iii) Bradley's article entitled "The snow resistograph and slab avalanche investigations." In *International Symposium on Scientific Aspects of snow and Ice Avalanches*, Davos, Switzerland, 5–10 Apr. 1965, International Association of Hydrological Sciences, International Union of Geodesy and Geophysics, Publ. No. 69, p.251–260; iv) Dowd et al. 's article entitled "A new instrument for determining strength profiles in snow cover." Journal of Glaciology, 32(111):1986, pp.299–301; and v) Vogel's German patent application entitled "Schneeprofilmessonde," Offenlegungsschrift DE 19503017A1, 1995.

Existing penetrometers have large diameter penetrating tip sections with shallow angles greater than 30°. These tips penetrate snow surfaces by producing bulk snow collapse and pushing a snow mass in front of a penetrating tip. This phenomenon is taught in the article by Fritton entitled "A standard for interpreting soil penetrometer measurements" in Soil Science, 105(2) : pp.542–551 1990. Snow mechanical behavior depends strongly on the degree of bonding between snow grains and it is unclear how the complex deformation field of the bulk snow collapse around a large penetrating cone relates to the inter-grain bonding. When a snow body forms on the cone, the shape of the penetrating tip changes and the failure surface is not at the metal snow. interface, thus yielding spurious data measurements. Also, thin weak layers within a snow cover may be important initiation regions for determinations whether avalanches are probable. Large diameter cones have poor resolution and unable to detect layers less than about 3 cm, see Bader et al.'s article entitled Snow and its Metamorphism 1954, p.135.

Existing hand driven penetrometer devices accumulate significant stored energy in the muscles of the body of the user. This energy can be released suddenly when the snow strength changes during a test. In addition, the velocity of insertion can be variable depending upon the individual conducting the test. The invention herein minimizes the problem of stored energy and variable penetration speed by using a high modulus penetrometer device whose penetration speed remains constant.

Moreover, these devices with small diameter penetrating tips are not flared and are installed near the penetrometer drive head. Consequently, their measurements can be affected by friction with the snow behind the penetrating tip and a snow body that is pushed ahead of the drive head. In contrast, the instant invention's penetrating tip is flared whose tip is extended beyond the drive head. Thus, measurement errors related to friction and a snow body in front of the drive head are minimized. The invention's blade penetration tip design maintains the advantages of a small width penetration tip while intercepting many snow grain bounds in a coarse large grained snow by an increased blade length of the tip.

Additionally, these devices determine penetrating force data only without regard to the resolution of this data. The lack of resolution prevents further frequency analysis of such data to determine actual snow grain size as by the instant invention. Additionally, the instant invention continuously records this penetrating force the data to achieve this grain size determination.

The problems discussed above are resolved by the instant invention by use of a very thin penetrometer tip section using various tip designs that are less than 5 mm in thickness and extended beyond a penetrating head. These structural features obviate problems a associated with frictional snow formation during a penetrometer push operation yielding improved data results.

SUMMARY & OBJECTS OF THE INVENTION

The snow penetrometer apparatus with data acquisition hardware measure force required to push a small dimension tip member into a snow surface at constant speed that: i) is less than 5 mm in diameter or cross-sectional width, ii) has up to a 90° included angle; iii) has a flared tip and iv) is extended beyond a penetrating head. The penetrometer tip member has a high elastic modulus and is attached through a connecting rod to a stiff penetrating head that is in turn attached to a driving rod. The penetrometer tip member acts through a force sensing transducer. The driving rods are a meter in sectional length that can be joined together for snow penetration up to several meters. The depth of snow penetration is determined by measuring movement of a drive motor or drive rods. The penetrometer tip member is driven downward by a constant speed rotary or linear motor. Two different penetrating head designs are used. The first penetrating head design has a diameter slightly larger than the driving rod to reduce sidewall friction. The second penetrating head design has the same diameter as the driving rod to reduce the volume of influence ahead of the penetrating head. Both heads are low including angle of 30° or less. A measured event of the penetrometer tip encountered force is recorded and correlated with depth of penetration for later analysis to determine its mean value and variation about this mean value to obtain an index measure of inter-grain bounding and snow grain size.

Accordingly, several objects of the present invention are:

To provide a snow penetrometer measurement device with an improved tip member structure that reduces frictional effects during a penetration push operation resulting in a cone of snow material being pushed in front of the penetrating tip thereby reducing the resolution of thinner snow layers being observed, which in turns provides improved data of an index of snow grain bond strength and snow grain size;

To provide a snow penetrometer measurements device with an improved combined penetrating drive head/tip member structure ahead of the driving rod head that minimizes the influence of a snow body pushed in front of the drive rod head during a penetration push measurement; and To provide a snow penetrometer measurement apparatus for providing consistent and high resolution force versus depth measurement data that combines a elastic modules penetration tip member with a constant speed drive unit for constant penetration rates.

Still further advantages will become apparent from consideration of the ensuing detailed description and drawings.

BRIEF DESCRIPTION OF THE DRAWING

FIG. 3A shows a side view of a constant speed motor of the snow penetrometer measurement device shown in FIG.2B.

FIG. 3B shows a side view of an exploded view of the top of the drive shaft and sleeve members of the snow penetrometer measurement device shown in FIG.2B for insertion and attachment to motor shown in FIG.3A.

FIG. 3C shows a side view of the individual drive members of the snow penetrometer measurement device shown in FIG. 2B.

DETAILED DESCRIPTION OF THE INVENTION

Figure 1A:
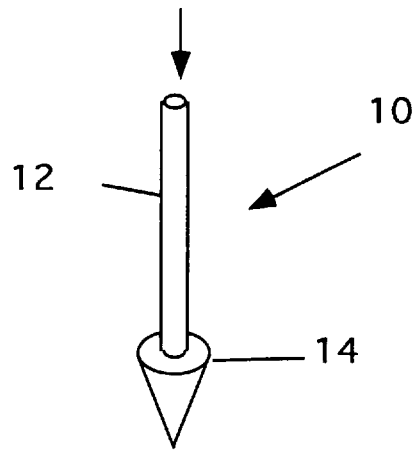
FIG. 1A shows a perspective view of a cone penetrometer tip driven at a constant penetration speed into a snow surface.
Figure 1B:
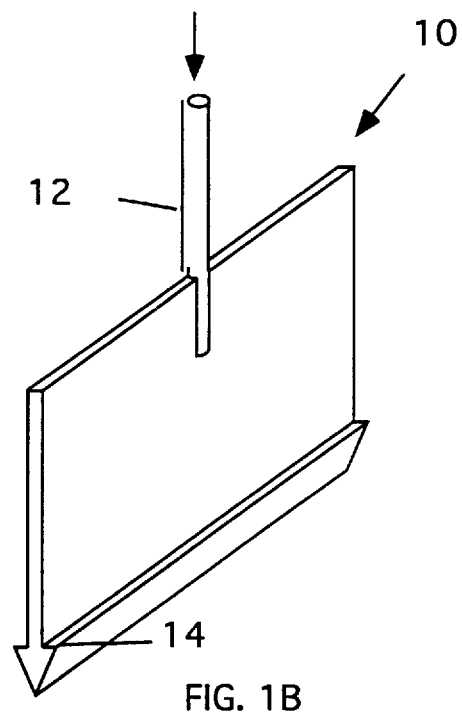
FIG. 1B shows a perspective view of a blade penetrometer tip driven at a constant penetration speed into a snow surface.
Figure 1C:
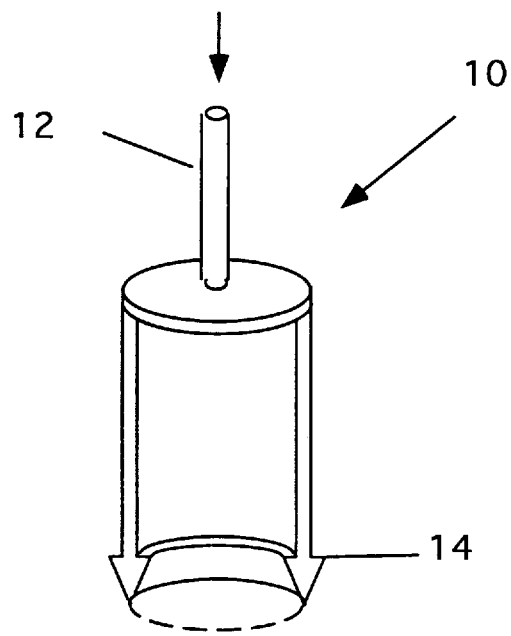
FIG. 1C shows a perspective view of cylindrical annulus penetrometer tip driven at a constant penetration speed into a snow surface.
Figure 2A:
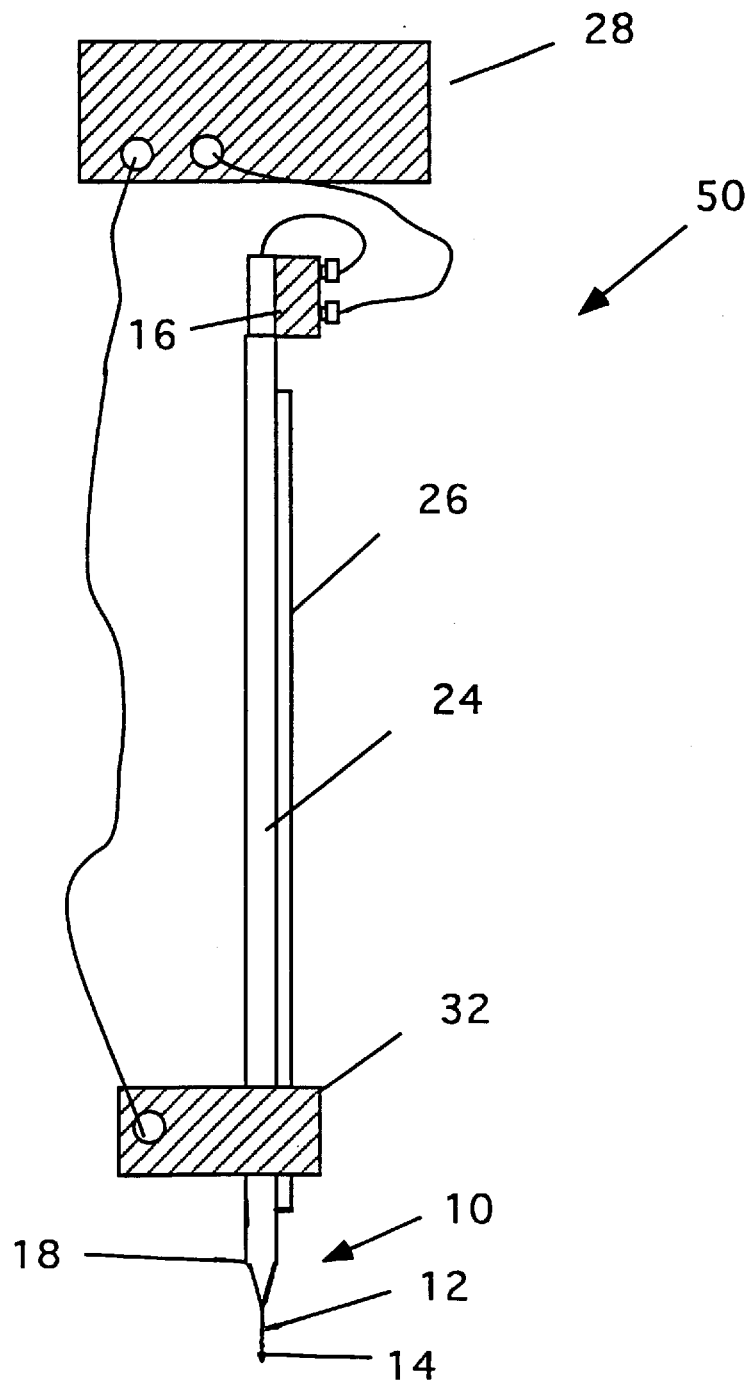
FIG. 2A shows a side view of a snow penetrometer measurement device driven through an externally mounted rack by a motor.
Figures 2B, 2C:
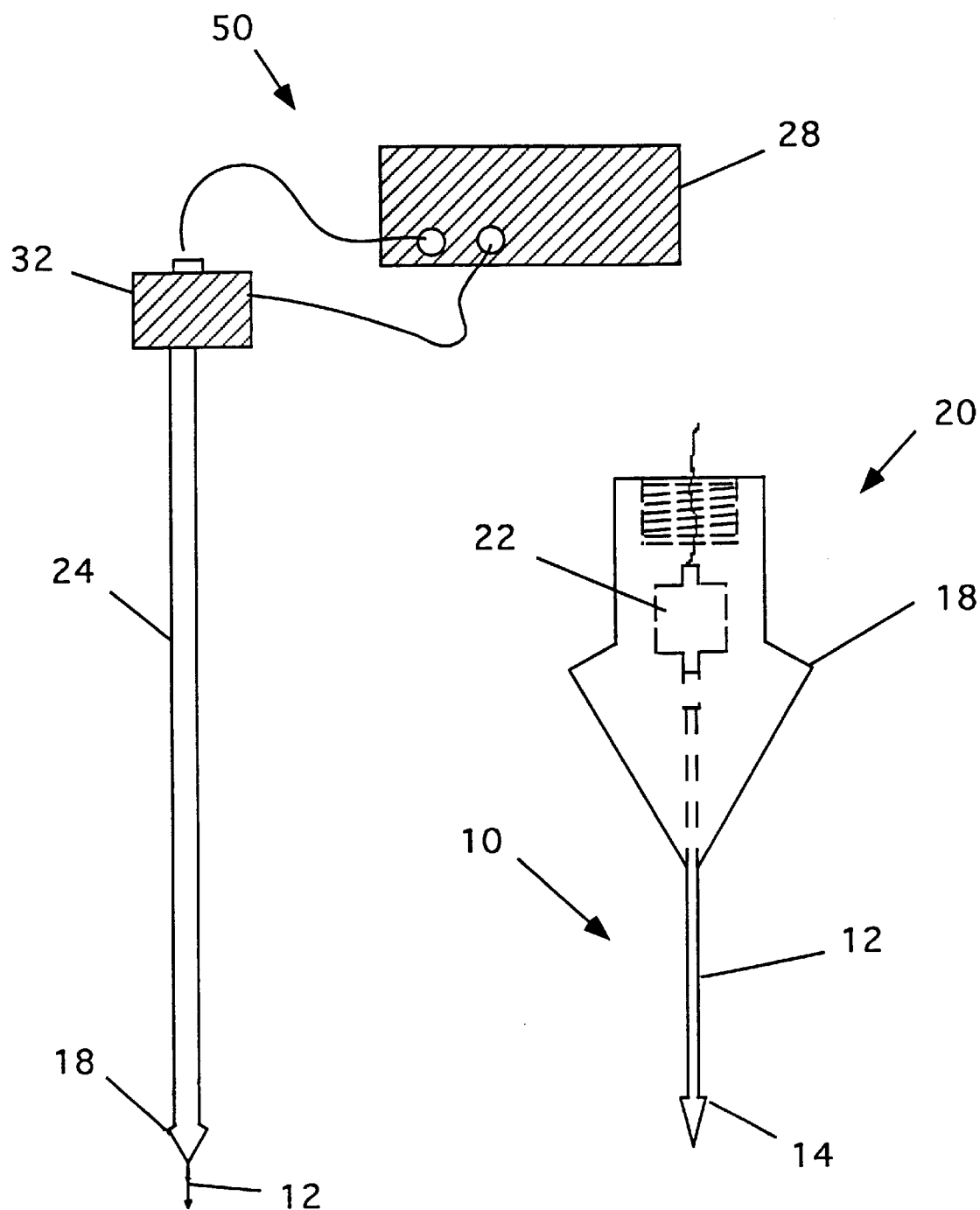
FIG. 2B shows a side view of a snow penetrometer measurement device driven by an internal threaded drive shaft by a motor.
FIG. 2C shows a side view of an exploded view of the drive head with tip section with the force transducer disposed therein.

FIGS. 1A, 1B, 1C show penetrometer tip 10 designs through a connecting rod 12 for use in the devices shown in FIGS. 2A and 2B that measure snow resistance. Extreme flare dimension 14 of the the penetrating drive tip 10 is less than 5 mm with a standard 30° angle shown although up to a 90° angle can be used. Penetrating tip dimensions are designed to be as small as possible, limited only by the requirement that the tip penetrate snow without undergoing significant deformation, thus allowing tip interaction with as few grains as possible across the tip's diameter or width. Tip 10 designs of FIGS. 1A, 1B and 1C can detect thin snow layers. Depth of snow penetration can be increased by increasing the strength of drive rod 24 and motor 32. Penetrometer tip flare 14 is used to reduce the influence of friction. Practical tip dimensions with a diameter or width that is less than 5 mm have been used to obtain an accurate measure of inter-grain bonding and snow size and detect thin snow layers. Small tip dimension 14 and small included angle minimize the compaction of snow and the formation of a snow body ahead of the penetrometer, as often occurs when using larger diameter snow penetrometer devices that may have high included angle that are greater than 30° in snow. This phenomenon of particulate material is taught in Huang et al.'s article entitled "A micro-mechanical study of penetration tests in granular material," Mechanics of Materials, 16(1&2): pp. 133–139, 1993. The extension length from the penetrating head 20 to the penetrating drive tip 10 is at least one diameter of the maximum dimension of the driving head 18 to reduce the effects of snow compaction produced by the penetrating drive rod. The ratio of the extension length of the connecting rod 12, connecting the penetrating head 20 to the penetrating drive tip 10, to the diameter of the maximum width of the driving head 18 is greater than one, to reduce the effects of snow compaction produced by the penetrating drive rod. The tip member it, is made of either titanium, stainless steel, composite material or high strength aluminum alloy.

The blade penetrating drive tip 10 shown in FIG. 1B contacts few snow grains across its width but contacts many grains along its length. Blade resolution can be changed by variations to the transverse length of the blade that is parallel to the tip flare portion 14. The blade penetrometer tip 10 allows for measurements of thin snow layers which can be delineated to high resolution.

The cylindrical annulus penetrating design drive tip 10 in FIG. 1C with the bottom half cut away can penetrate to several hundreds of mm. The cone contacts few grains of snow across its diameter. The small dimension of the cone results in its intercepting few snow grains during penetration allowing the properties of individual snow grain structures to be measured. The blade and cone are attached to connecting rod 12 for continuous penetration of several meters. The cylindrical annulus penetrating drive tip 10 is several hundred of millimeters in height and very thin at flare tip 14, i.e. less than 5 mm.

A constant speed high modulus penetrometer head 20 is used to minimize the effects of penetration speed and stored energy on measured penetration force. Low penetration speeds may result in rate dependent visco-plastic deformation while high penetration speeds may be affected by inertia. At intermediate penetration speeds, in the range of 0.2–40 cm/s, snow compaction and penetration is relatively insensitive to penetration or compaction speed. Snow bonds appear to fail by brittle fracture without significant inertial effects.

Excessive stored energy in a penetrometer can produce erratic measurements as the penetrometer recoils after each snow compaction or failure event. The amount of stored energy depends on the elastic distortion in the penetrometer which for a constant speed motor driven device is controlled by the effective modulus of the penetrometer, force transducer and motor assembly. A high modulus assembly minimizes stored energy effects as provided for by the invention's design.

FIGS. 2A and 2B show two snow penetrometer measurement devices 50 with the stationary frame and motor 32 and control, data acquisition 28, transducer amplification unit 16. The penetrometer measurement devices 50 shown in FIG. 2A is driven through an externally mounted rack 26 which is attached to the drive rod 24 using a constant speed motor 32. The motor 32 is attached to a rigid frame that is statically positioned at the snow surface where measurements are made. The rigid mounting frame of the motor 32 such that the penetrometer tip 10 can be driven into the snow can be configured to several mounting structures that include to a mobile vehicle, to skies when used as a portable unit for ski patrols in avalanche regions, or fixed to a metal Frame rigidly attached to a foundation in the ground for the monitoring snow properties.

The motor 32 can be either a constant speed rotary motor with a constant speed drive controller or a linear actuator motor. A rotary or linear displacement encoder is part of the motor 32 and connected to the data acquisition hardware 28 to correlate depth of penetration measurements with tip force encountered during a penetration operation. Both a non-flared and flared drive head 20 are shown in FIGS. 2A and 2B respectively. The force transducer 22 is shown in exploded view of FIG. 2C which is the transduction element for measuring penetrating force. A typical force transducer 22 with amplifier 16 are a Kistler piezo-electric force transducer type 9203 with a miniature charge amplifier Kistler 5039A 212 unit or an Interface SM 250 strain gauged load cell. An apparatus 50 with depth capabilities of several hundred millimeters would use a limited drive penetrometer unit with a drive motor 32 being a linear motor such as Industrial Drives linear actuator D1208A-G-MXC-MT1-Q. A stepper rotary motor that can be used is a SAIA UFB3 with J-gear two-phase stepper motor.

The penetrometer measurement device 50 in FIG. 2B is driven by an internal threaded drive shaft 36 as shown in detail in FIGS. 3A,3B and 3C using a top mounted constant speed motor 32. This design prevents the drive mechanism from becoming clogged with snow. The stationary sleeve 38 fits in the drive shaft 36 and is prevented from rotating by the central motor plug 46. The drive shaft 36 is threaded into the penetrometer drive tube 34. The drive tube 34 is attached to the penetrometer drive head 20 as appears in exploded view FIG. 3B. The penetrating drive tip member 10 is driven by the top mounted motor 32 which is rigidly mounted to a rigid frame positioned at the snow surface. The motor 32 produces rotation in the drive shaft 36. The data acquisition unit 28 is for example an IOtech, model Daqbook/100 or a Campbell Scientific, Inc. model CR10 data unit. A portable personnel computer (PC) with parallel interface can be used for control and storage of the data. The PC is programmed with standard well known programming languages for data acquisition and control.

Force versus depth of penetration of the tip section 10 have resolution capabilities of ±500 newtons with ±1% accuracy depending upon required data needs. The force resolution can be further increased by changing the transverse blade length of blade tip member 10 shown in FIG. 1B. Depth resolution 0.05 mm when using a constant speed rotary motor and $10^{-3}$ mm when using a linear actuator motor. The penetration data of force versus depth using a small penetrating tip dimension allows for accurate determination of mean penetrating force and snow grain size. The mean strength of bond between snow grains is directly related to the mean penetration force. Grain size and spacing information is determined by the frequency an magnitude of the force variation about a mean penetration force. Coarse grained snow has large grain size and more void space between grains when compared to fine grained snow at the same density. When the tip 10 is moved at constant speed, the force of impacting a large grain (more mass) is greater compared to when it impacts a small grain. The impacts will also be lower because separation of grains is greater between large grains than small grains for the same density. The relationship between frequency and force variation magnitude and grain size is determined by doing time varying Fourier analysis or a wavelet analysis to resolve frequency versus power (magnitude) information as a function of penetration depth, see Olsen's article entitled "Sensing of aggregate size by means of horizontal mini-penetrometer," in *Soil & Tillage Research*, 24 (1992) pp.79–94.

Other possible uses of snow penetrometer device 50 includes determining penetration resistance of foams, comparable structured materials, aggregates with link matrixes or cellular food products. The tip design 10 can be used as a substitute tip member device in other snow measuring devices.

While this invention has been described in terms of specific embodiments, it is understood that the invention is capable of further modification and adaptation following in general the principle of the invention and including such departures from the present disclosure as (some within the known or customary practice in the pertinent arts and may be applied to the central features set forth, and fall within the scope of the invention and of the limits of the appended claims.

We claim:

1. A snow penetrometer measurement apparatus comprising:

a penetrating drive tip member that is less than 5 millimeters in dimensional thickness with respect to a transverse penetration direction of a penetrated snow surface, the tip member has an included tip angle less than 90°, the tip member is attached through a connecting rod to a drive head member, a force transducer element that is disposed within the drive rod head member and is coaxially attached to the penetrating drive tip member thereby measuring normal force exerted by a subsurface snow formation, a drive rod member that is attached to the drive rod head member, a motor drive device is mechanically coupled to the drive rod member and held stationary by a rigid frame device that is statically positioned at the snow surface, the motor drive device is electrically attached to a constant speed motor controller unit, and a data acquisition system that is electronically coupled to the force transducer element that transduces the normal force exerted by the subsurface snow formation and includes a means for correlating subsurface depth.

2. The snow penetrometer measurement apparatus of claim 1 wherein the penetrating drive tip member is a flared tipped cone penetrometer.

3. The snow penetrometer measurement apparatus of claim 1 wherein the penetrating drive tip member is flared tipped blade penetrometer.

4. The snow penetrometer apparatus of claim 1 wherein the penetrating drive tip member is a flared tipped cylindrical annulus penetrometer.

5. The snow penetrometer measurement apparatus of claim 1 wherein the length from the drive head to the penetrating drive tip is at least one diameter of a maximum dimension of the driving rod head member thereby reducing the effects of snow compaction produced by the drive rod member.

6. The snow penetrometer measurement apparatus of claim 1 wherein the drive rod head member approximately has the same cross-sectional dimension as the drive rod member.

7. The snow penetrometer measurement apparatus of claim 1 wherein the drive rod member is attached lengthwise to a rack member that is mechanically coupled to the drive motor.

8. The snow penetrometer measurement apparatus of claim 1 wherein the drive rod member is an internal threaded drive shaft driven by the drive motor, a stationary sleeve is telescoped in the drive shaft and is prevented from rotating by a central motor plug disposed in the central section of the drive motor, the drive shaft is threaded into a penetrometer drive tube that is attached to the drive rod head member thereby preventing the drive rod member from becoming clogged with snow.

9. The snow penetrometer measurement apparatus of claim 1 wherein the drive rod head member is flared.

10. The snow penetrometer measurement apparatus of claim 1 wherein the drive rod head member is non-flared.

11. The snow penetrometer measurement apparatus of claim 1 wherein the penetrating drive tip member is made of a material selected from the group consisting of titanium, stainless steel, composite material or high strength aluminum alloy.

12. The snow penetrometer measurement apparatus of claim 1 wherein the motor drive device is a constant speed rotary motor.

13. The snow penetrometer measurement apparatus of claim 1 wherein the motor drive device is a linear motor.

14. A tip device for a snow penetrometer comprising:

a penetrating drive tip member 10 that is less than 5 millimeters in dimensional thickness with respect to a transverse penetration direction of a penetrated snow surface, the tip member has an included tip angle less than 90°, the tip member is attached through a connecting rod 12 to a drive rod head member 16, a force transducer element that is disposed within the drive rod head member and is coaxially attached to the penetrating drive tip member thereby measuring normal force exerted by a subsurface snow formation and minimizes the influence of a snow body pushed in front of the drive rod head during a penetration push event.

15. The snow penetrometer measurement apparatus of claim 14 wherein the penetrating drive tip member is a flared tipped cone penetrometer.

16. The snow penetrometer measurement apparatus of claim 14 wherein the penetrating drive tip member is a flared tipped blade penetrometer.

17. The snow penetrometer measurement apparatus of claim 14 wherein the penetrating drive tip member is a flared tipped cylindrical annulus penetrometer.

18. The snow penetrometer measurement apparatus of claim 14 wherein the length from the drive head to the penetrating drive tip is at least one diameter of a maximum dimension of the driving rod head member thereby reducing the effects of snow compaction produced by the drive rod member.

19. The snow penetrometer measurement apparatus of claim 14 wherein the drive rod head member approximately has the same cross sectional size dimension as the drive rod member.

20. The snow penetrometer measurement apparatus of claim 14 wherein the drive rod head member is flared.

21. The snow penetrometer measurement apparatus of claim 14 wherein the drive rod head member is non-flared.

22. The snow penetrometer measurement apparatus of claim 14 wherein the penetrating drive tip member is made of a material selected from the group consisting of titanium, stainless steel, composite material or high strength aluminum alloy.

* * * * *